United States Patent [19]

Taylor

[11] Patent Number: Plant 7,176

[45] Date of Patent: Mar. 6, 1990

[54] NECTARINE—LATE RED JIM

[75] Inventor: James W. Taylor, Dinuba, Calif.

[73] Assignee: Ito Packing Co., Inc., Reedley, Calif.

[21] Appl. No.: 283,989

[22] Filed: Dec. 13, 1988

[51] Int. Cl.[4] ..... A01H 5/00

[52] U.S. Cl. ..... Plt./41

[58] Field of Search ..... Plt. 41

*Primary Examiner*—James R. Feyrer

*Attorney, Agent, or Firm*—Dennis B. Haase

[57] ABSTRACT

A new and distinct variety of nectarine tree characterized by a yellow fleshed, cling stone fruit, which is attractive in appearance and having excellent sugar content and flavor, and, further, having the characteristic and advantage of maturing in the latter part of the late season, thereby becoming marketable at a time when comparable fruit is likely to be less available.

1 Drawing Sheet

BACKGROUND OF THE VARIETY

The present invention relates to a new and distinct variety of nectarine tree, which I refer to as "Late Red Jim", of a yellow fleshed, cling stone fruit, attractive in appearance, maturing in the late season period, which was developed from a continued fruit breeding program.

ORIGIN AND ASEXUAL REPRODUCTION OF THE NEW VARIETY

This novel nectarine was derived from an ongoing fruit breeding program to the improvement of nectarines to enhance quality and market acceptability. The flowers of the Red Jim variety (U.S. Plant Pat. No. 4,518) were emasculated and pollenated with pollen from the variety May Grand (U.S. Plant Pat. No. 2,794). Seeds produced from this method were stratified and grown to a height of about 18 inches. These seedlings were bud grafted into dehorned orchard trees in the experimental orchard of Ito Packing Co., Inc., Reedley, Calif., for testing and selection. Each clone was budded into several limbs to make sure that it propagated true to type.

SUMMARY OF THE NEW VARIETY

The instant variety developed through the above method was selected because of its uniquely deep red color of skin, good flavor, aroma and texture, which contributes to its exceptional eating quality. The novel nectarine of the present invention has a much more attractive red color than other varieties ripening at the same period and a maturity date of approximately three weeks later than a similar variety, which is the subject matter of a copending application.

BRIEF DESCRIPTION OF THE DRAWING

The accompanying drawing illustrates typical specimens of the fruit and foliage of my new variety as grown in the San Joaquin Valley of California. Two specimens are shown, one of which is in the side elevation and the other from the apex view; yet another specimen is a section side elevation illustrating the internal texture and color of the flesh and pit.

DETAILED DESCRIPTION

The following is a detailed description of my new variety. Each color reference is with respect to the Maerz and Paul Dictionary of Colors, except in instances where terminology having generally accepted meaning is employed.

Parentage: Red Jim × Unnamed selection F1.

Propagation: Maintains its distinguishing characteristics through several bud grafts.

Locality where grown and observed: Near Reedley, County of Fresno, Calif.

TREE

Size: Large, vigorous, spreading, open, vase form.

Vigor: Vigorous, productive.

Regularity of bearing: Regular bearer.

Trunk: Medium size; medium texture.

Branches: Spreading.

Leaves:

- *Color.*—Top side — 32B9; underside, 311B.
- *Size.*—Average length — 5.2 inches; average width 1.4 inches, medium thickness.
- *Petiole.*—Medium length; medium thickness.
- *Glandular characteristics.*—Average number — four; opposite; medium size; reniform, position — usually two on at the base of the leaf blade near the attachment of the petiole and occasionally one on the petiole near the leaf blade.
- *Stipules.*—Dehiscent in early stage of development.

Flower bud: Medium size.

Flower: Large, showy.

- *Color.*—Pink.
- *Anthers.*—Red.

Time of full bloom: With variety Red Jim (U.S. Plant Pat. No. 4,518).

FRUIT

Maturity: When described, firm ripe, Aug. 15, 1988.

Date of first picking: Aug. 15, 1988.

Date of last picking: Aug. 30, 1988.

Size:

- *Average axial length.*—3⅛ inches; average transverse width in suture plane — 3 inches.
- *Axial diameter.*—About 3 inches.

Form: Essentially round but compressed at the base. Often slightly larger on right half but may be larger on left half of the fruit from the ventral suture.

- *Tendency of crack.*—None observed.
- *Suture.*—Shallow in lower one-third of fruit but deepens in the upper one-third of the ventral suture to the point where the apex is below the contour of the fruit; dorsal suture present but very shallow except near the apex where it deepens to meet ventral suture.

Ventral surface: Smooth.

Cavity: Round, deep (average 7/8 inches), narrow, with small area of stem attachment.

Base: Flatened slightly.

Apex: Smooth with little or no point, recessed with the suture, sometimes slightly curled.

Skin:

*Thickness.*—Medium thick; medium texture.

*Tendency to crack.*—None observed.

*Bloom.*—Wanting.

*Color.*—Base color yellow (11L2) but only around the base of the fruit where it is pressed against the limb. Lighter portions light orange (9LB), heavily speckeled with red (5L5) over most of the surface. Much of the surface of red color (6L5) which deepens to a very darker red (55L4) as the fruit matures.

Flesh:

*Texture.*—Very firm, meaty.

*Color.*—Yellow with slight redish tinge (9L1). considerable red around the pit extending through much of the flesh (5L7).

*Juice.*—Abundant.

*Fibers.*—Considerable around pit with many running out into the flesh.

*Ripening.*—Even. Stays firm on the tree for a long time after maturing.

*Flavor.*—Good balance of acid and sugar. Sweeter than many nectarines at this season.

*Aroma.*—Not very pronounced.

*Eating quality.*—Excellent.

Stone:

*Adherence to flesh.*—Cling stone.

*Size.*—Average thickness $\frac{3}{4}$ inch; average width 1 inch; average length $1\frac{1}{8}$ inches.

*Form.*—Oval.

*Hilum.*—Small, oblong.

*Dorsal edge.*—Shallow grooves, often breaking away to deep groove where one-half of pit on either side of suture is larger than the other.

*Ventral edge.*—Narrow, very little wing toward the apex.

*Surface.*—Irregular broad grooves, deeper than in most varieties.

*Color.*—Brown (7L12) shaded to reddish brown throughout (47L1).

*Tendency to split.*—Seldom.

Use: Fresh market.

Keeping quality: Excellent.

Shipping Quality: Excellent.

Resistance to disease: Similar to other glanded varieties of nectarines.

Although this novel variety of nectarine possess the described characteristics as a result of the growing conditions in the Reedley area of Fresno County, Calif., in the central portion of the San Joaquin Valley, it is to be understood that variations of the usual magnitude in characteristics incident to growing conditions, fertilization, pruning and pest control are to be excepted.

Having thus described and illustrated my new nectarine tree, what is claimed as new and desired to be secured by Letters Patent is:

1. A new and distinct variety of nectarine tree with fruit of yellow flesh, cling stone type, substantially as herein shown and described, having a maturity period in the latter part of the late season, having fruit with good sugar content, the fruit being large with skin of a deep red color over much of the exterior, and flesh of a firm texture with good flavor.

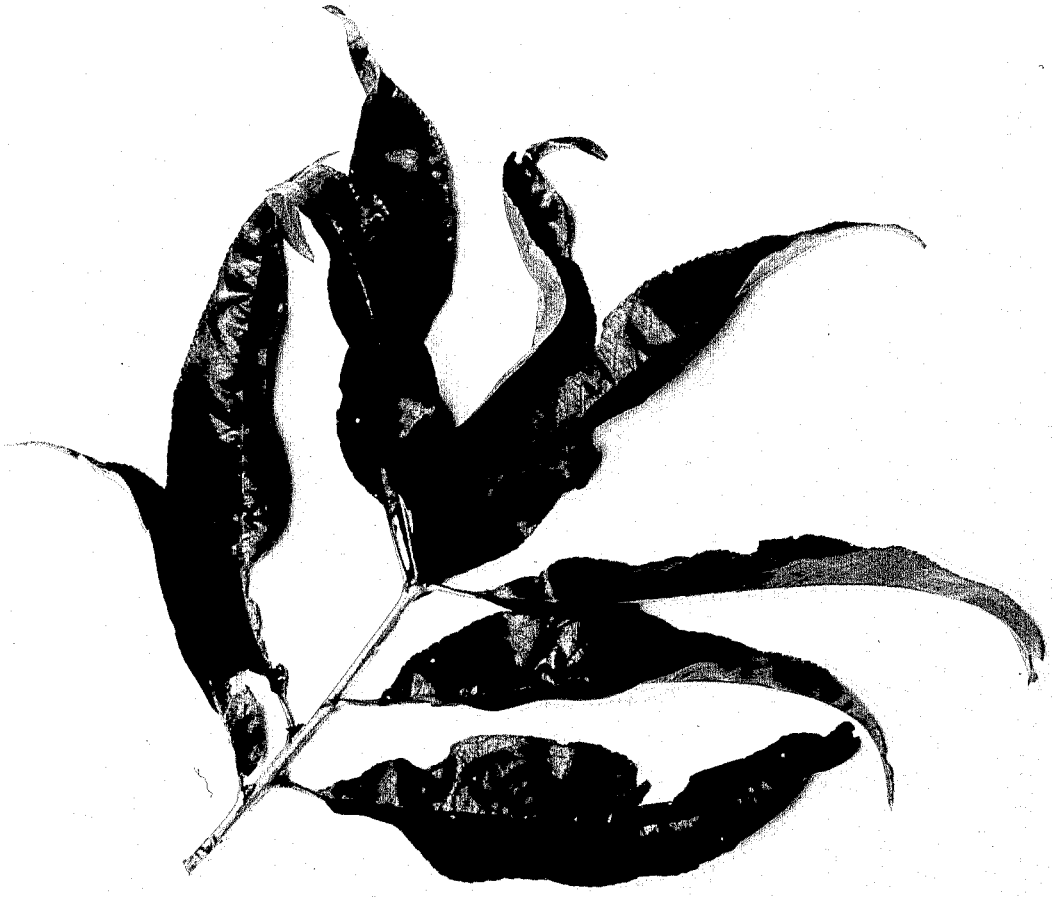
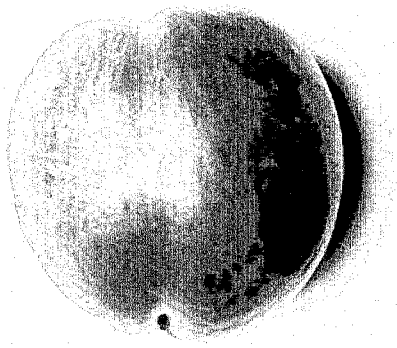
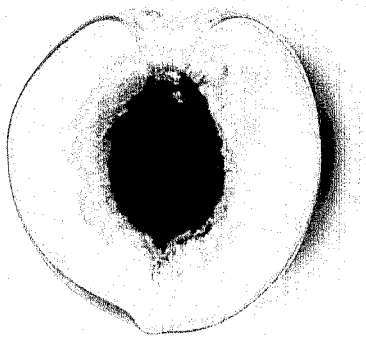
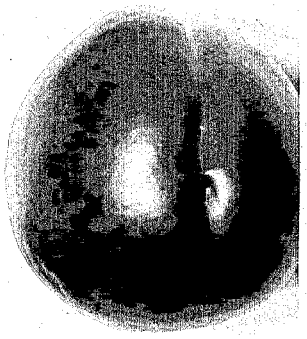

* * * * *